United States Patent [19]
Wilson et al.

[11] Patent Number: 5,714,384
[45] Date of Patent: *Feb. 3, 1998

[54] COMPARTMENTALIZED TISSUE CULTURE BAG

[76] Inventors: John R. Wilson, 173 Windsor La., New Brighton, Minn. 55112; Martin L. Wolf, 1280 Keston St., St. Paul, Minn. 55108

[*] Notice: The term of this patent shall not extend beyond the expiration date of Pat. No. 5,693,537.

[21] Appl. No.: 413,335

[22] Filed: Mar. 30, 1995

Related U.S. Application Data

[63] Continuation-in-part of Ser. No. 268,073, Jun. 28, 1994, abandoned.

[51] Int. Cl.[6] .................. C12N 5/00; C12M 3/06
[52] U.S. Cl. .................. 435/401; 435/297.1; 435/297.5; 435/304.2
[58] Field of Search .................. 435/240.1, 240.2, 435/240.23, 240.24, 240.25, 288.1–288.5, 297.5, 304.1–304.3, 305.1–305.4, 399, 401, 402

[56] References Cited

U.S. PATENT DOCUMENTS

| | | |
|---|---|---|
| 3,597,326 | 8/1971 | Liner . |
| 4,012,288 | 3/1977 | Lyman et al. . |
| 4,296,205 | 10/1981 | Verma . |
| 4,599,315 | 7/1986 | Terasaki et al. . |
| 4,661,455 | 4/1987 | Hubbard .................. 435/285 |
| 4,748,124 | 5/1988 | Vogler . |
| 4,839,292 | 6/1989 | Cremonese .................. 435/311 |
| 4,937,196 | 6/1990 | Wrasidlo et al. .................. 435/284 |
| 5,068,195 | 11/1991 | Howell et al. .................. 435/284 |
| 5,153,131 | 10/1992 | Wolf et al. .................. 435/284 |
| 5,225,346 | 7/1993 | Matsumiya et al. .................. 435/284 |

FOREIGN PATENT DOCUMENTS

| | | |
|---|---|---|
| 0155237 | 9/1985 | European Pat. Off. . |

OTHER PUBLICATIONS

GIBCO BRL Catalogue & Reference Guide (1992) pp.7–9 and 78, 1992.
"Diffusion in Tissue Cultures on Gas–permeable and Impermeable Support", Mona D. Jensen, J. theor. Biol. (1976) 56, 443–458.
"Factors affecting cell growth and monoclonal antibody production in stirred reactors", S. Reuveny, et al., Journal of Immunological Methods, 86 (1986) 53–5.
Original Articles, Dec. 16, 1967, 1279–1281.

*Primary Examiner*—William H. Beisner
*Attorney, Agent, or Firm*—Sprung Kramer Schaefer & Briscoe

[57] ABSTRACT

A compartmentalized cell culture bag comprising a cell culture compartment defined by lower gas permeable film and an upper membrane selectively permeable to compounds of selected sizes. Culture medium resides between the upper membrane and the lower gas permeable film. A basal medium compartment is located above the upper membrane and allows basal medium to reside upon the upper membrane. Each compartment contains an access port. A gas film support below and in partial contact with the gas permeable film holds the gas permeable film in a substantially horizontal position so that suspension or adherent cells can distribute across the surface of the gas permeable film.

18 Claims, 7 Drawing Sheets

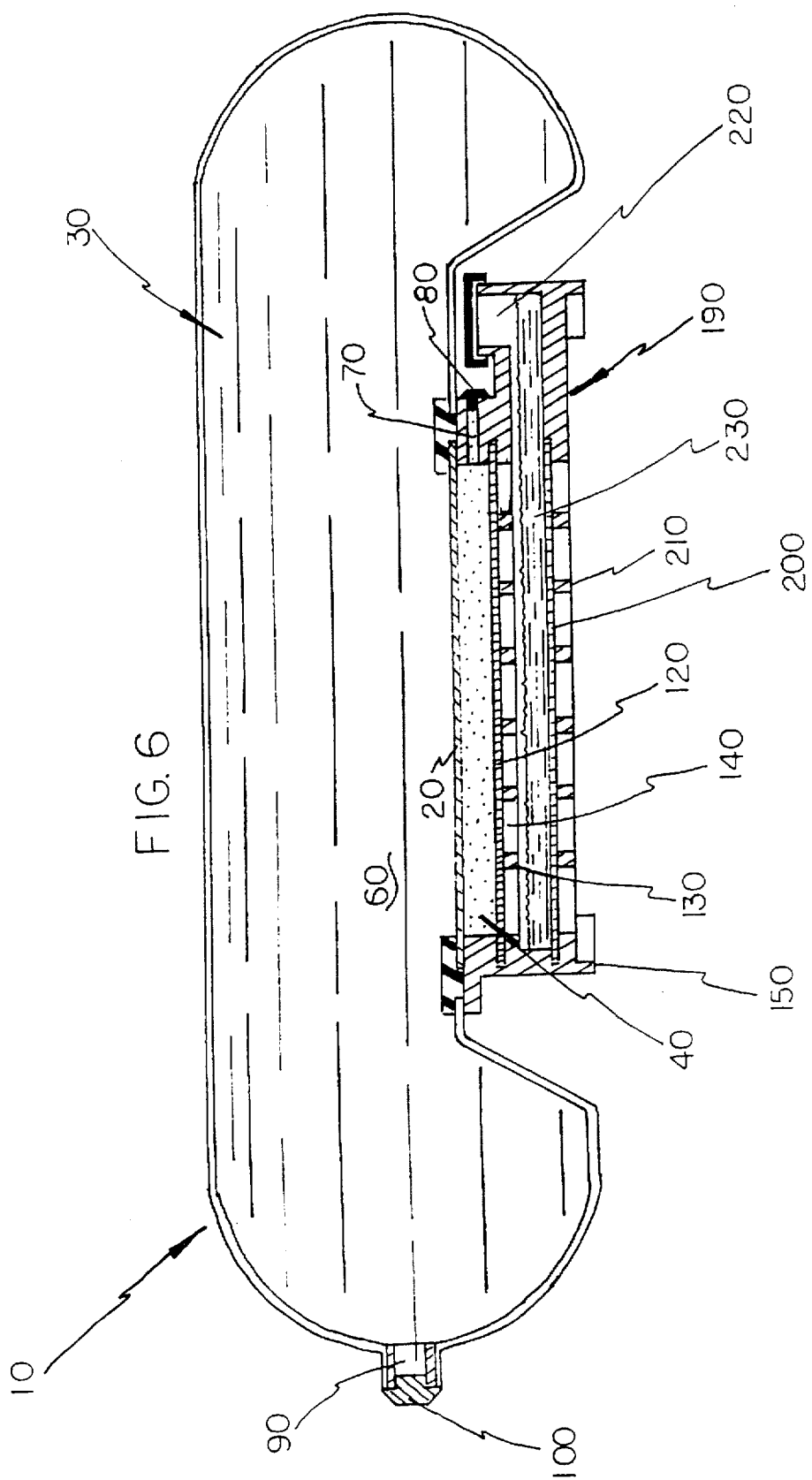

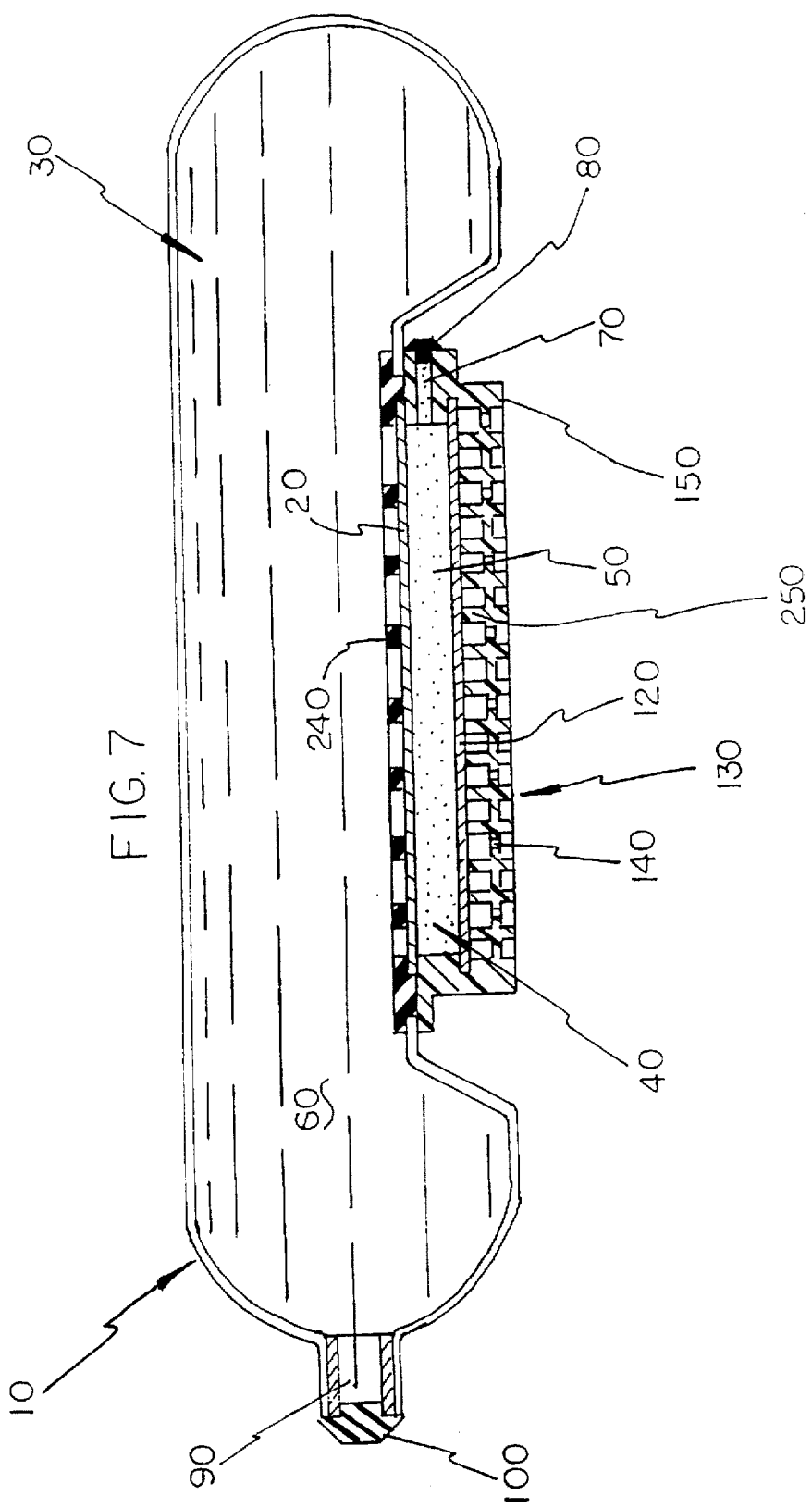

COMPARTMENTALIZED TISSUE CULTURE BAG

This is a continuation in part of application Ser. No. 08/268,073, filed Jun. 28, 1994, now abandoned.

BACKGROUND—FIELD OF THE INVENTION

This invention relates to a device and a method for growing cells or tissue in vitro.

BACKGROUND—DESCRIPTION OF PRIOR ART

In vitro growth of mammalian cells can be conducted in static culture vessels such as Lifecell™ bags (Baxter Travenol) SteriCell™ bags (DuPont). These culture devices are popular because they are easy to use and rely upon passive diffusion to support the metabolic demands of the cells. In this type of culture, a portion of the cell culture medium is periodically removed from the bag and replaced as cells consume nutrients and produce waste products. This protocol leads to the disadvantages of limited cell density, limited cell secreted product concentration, and periodic shifts in nutrient concentration.

To overcome these disadvantages, cells and cell secreted products need to be retained in the culture vessel when nutrients are replenished. Marbrook used a dialysis membrane to separate cells and cell secreted products from the basal medium, allowing passive diffusion to meet the metabolic demands of the cells (Marbrook, J., "Primary Immune Response in Cultures of Spleen Cells", the Lancet, 2, 1279–1281 [1967]). In this device, an inner concentric chamber resides within an outer concentric chamber. The bottom of the inner chamber is comprised of a dialysis membrane which is submerged in basal medium contained in the outer chamber. Cells reside on the membrane receiving nutrients and delivering waste products. Continuous dialysis becomes limited as the membrane loses substrate transport capacity due to the cell mass that resides upon it. Thus, the ability to carry out long term culture is compromised.

Verma (U.S. Pat. No. 4296,205 issued Oct. 20, 1981) teaches of the use of a tissue culture shelf placed in the cell culture compartment to keep cells from directly contacting and clogging the dialysis membrane. The tissue culture shelf has perforations to allow movement of nutrients to the cells. During the culture of suspension cells, the cells and cellular debris are capable of moving through the perforations and coming to rest upon the dialysis membrane, limiting continuous dialysis in long term culture. Also, the architectural structure of the shelf can lead to microenvironments as concentration gradients are unevenly distributed across the surface of the plate.

Vogler (U.S. Pat. No. 4,748,124 issued May 31, 1988) describes a cell culture compartment that is defined by a lower gas permeable, liquid impermeable sheet and an upper dialysis membrane. This configuration keeps the dialysis membrane from clogging as cells do not reside upon it, yet dialysis can become limited by other means. As with traditional cell culture bags, the configuration of Vogler limits the ability to vary oxygen tension relative to Marbrook and Verma. Furthermore, the surface chemistry of materials used to allow gas transfer are limited and in some cases can be undesirable for protein or cell contact. Finally, the teaching does not lead to high density cell culture relative to traditional static culture methods.

The architecture of Vogler can allow dialysis of the cell compartment to become limited. A problem can arise as liquid evaporates from the growth chamber. Vapor transmission across gas permeable surfaces can be substantial and the loss of liquid will lead to termination of dialysis as liquid contact with the dialysis membrane ceases.

In the traditional bag configurations as well as Vogler's, the gas permeable, liquid impermeable sheet of the cell culture compartment limits options available for controlling pericellular pH and $P_{O2}$. In the prior configurations of Marbrook and Verma, the oxygen tension could be varied by adjusting the liquid level of the cell culture compartment. The structure and method taught by Vogler require oxygen tension be varied by altering the ambient conditions of the atmosphere surrounding the device.

Oxygen tension is very important to cell viability and protein secretion (Reuveny et al., "Factors Affecting Cell Growth and Monoclonal Antibody Production in Stirred Reactors", Journal of Immunological Methods, 86, 53–59 [1986]). The gas permeability of commercially available liquid impermeable sheets and the impact upon pericellular pH and $P_{O2}$ is described in detail by Jenson et al. (Jenson M. D., Wallach D. F. H., and Sherwood P., "Diffusion in Tissue Cultures on Gas- permeable and Impermeable Supports", J. Theor. Biol. (1976) 56,443–458). The oxygen demands of various cell types combined with the gas permeability of various gas permeable, liquid impermeable sheets will dictate a specific steady state pericellular pH and $P_{O2}$ for each combination. This means cell lines are subject to very limited pericellular conditions. Creating different pericellular conditions is achieved by altering the ambient conditions of the incubator in which the device resides. As a practical matter, this is difficult for researchers who maintain incubators at standard conditions for a wide variety of simultaneous uses.

Gas permeable, liquid impermeable sheets also limit the surface chemistry available for support of cells and protein structures. The proliferation and function of many cell types is strongly affected by the chemical nature of the surfaces they reside upon. The surface chemistry of liquid impermeable material is incompatible with many cell types and protein structures. Also, hydrophobic material which is often the basis for gas permeable, liquid impermeable films, can cause non-specific protein binding. This in turn can lead to depletion of soluble growth factors. Thus, further modification to the materials may be required for optimization of the cell environment.

The architecture of Vogler also leads to limited cell density. The growth chamber will deform in shape due to the weight of liquid residing upon it and pressure of fluid expansion, leading to a sagging gas permeable sheet. This allows suspension cells to settle in the low point of the sheet. High localized cell densities at the low point of the sheet leads to excessive resistance to flux of nutrients and a localized reduction in cell viability. Furthermore, the cells are unable to expand to other areas of the gas permeable sheet.

It is accordingly an object of the present invention to provide a method and device in a compartmentalized cell culture bag format for the long term culture of anchorage dependent cells and suspension cells at high density, simultaneously allowing variable oxygen tension, an even distribution of cells across the bottom of the culture compartment, uninterrupted dialysis, and a wide variety of surface chemistry options. Advantageously, both the method and device will utilize passive diffusion to meet the metabolic demands of the cells. Still further objects and advantages will become apparent from consideration of the ensuing description and drawings.

SUMMARY OF THE INVENTION

Many of the problems of the prior art are solved by a compartmentalized cell culture bag constructed in accordance with this invention to allow cells to be cultured at high density over a long period of time.

There is provided a cell culture device comprising a container provided with a basal medium access port and an opening, an upper membrane selectively permeable to compounds of selected sizes and positioned across said opening, said container and said upper membrane together defining a basal medium compartment, a gas permeable film disposed below said upper membrane and with said upper membrane defining a cell culture compartment, access means between the inside of said cell culture compartment and outside thereof whereby cell culture can be introduced into and withdrawn from said cell culture compartment, and a gas film support below and in partial contact with said gas permeable film whereby at least a portion of said gas permeable film is held in a substantially horizontal position such that cells can distribute across the horizontal portion of said gas permeable film and gas can contact the underside of said gas permeable film.

For high density cell culture, the surface area of said upper membrane is at least one quarter of the surface area of said gas permeable film and the average distance between the substantially horizontal portion of said gas permeable film and said upper membrane is less than about 5 millimeters. The smallest cross-sectional area of said gas film support open to gaseous communication with the ambient environment is less than the total surface area of the underside of said gas permeable film in contact with gas.

In accordance with a preferred embodiment the cell culture compartment also includes an upper sheet having a surface area at least one quarter of the surface of the lower gas permeable film, and the distance between the substantially horizontal portion of the lower gas permeable film and the upper sheet is less than 15 millimeters.

In accordance with another feature the oxygen control compartment is open to said basal medium and adapted by appropriate means to allow a selected volume of said basal medium to reside in said oxygen control compartment.

According to a further feature of the invention, said gas permeable film includes sections which project into said cell culture compartment.

According to a further feature of the invention, said basal medium compartment includes a wall which is flexible.

According to a further feature of the invention, a gas exchange compartment connecting the inside top space of said basal medium compartment with the space below said gas permeable film limits evaporative loss from said cell culture compartment. The gas exchange compartment can be constructed to prevent basal medium from entering it and can include an access port for said gas exchange compartment whereby condensation can be removed and gas other than that of said basal medium compartment can communicate with the underside of said gas permeable film.

According to a further feature of the invention, oxygen tension within said cell culture compartment can be altered by including a second gas permeable film disposed in a horizontal position below first said gas permeable gas permeable film, providing a means separating first said gas permeable film from second gas permeable film to form a variable oxygen control compartment adapted to contain fluid, and an access port to said oxygen control compartment, whereby liquid can be added or removed to control the rate of gas transport.

With these structures, a method of culturing cells at high density becomes available. Also, a method of controlling oxygen tension surrounding cells becomes available by utilizing a liquid barrier to oxygen flux.

Thus there is provided a method of culturing cells in a device of the character described, comprising a) introducing a basal medium into said basal medium compartment, b) introducing cells and a cell culture medium into said cell culture compartment, and c) maintaining said cell culture compartmen at a predetermined temperature, whereby cells proliferate upon the upper surface of said gas permeable film and gas generated within said cell culture compartment passes through said gas permeable film.

With the invention so stated, problems associated with the prior art are solved. Long term, high density, in vitro culture of both suspension and adherent cells is possible with simultaneous provisions for variable oxygen tension, controlled evaporation, long term maintenance of small cell compartment liquid volumes, and uninterrupted dialysis.

A BRIEF DESCRIPTION OF THE DRAWINGS

FIG. 6 is a vertical cross-sectional view through an embodiment that allows variable oxygen tension; and FIG. 7 is a vertical cross-sectional view through an embodiment that limits the volume of the cell culture compartment.

Figure 1:
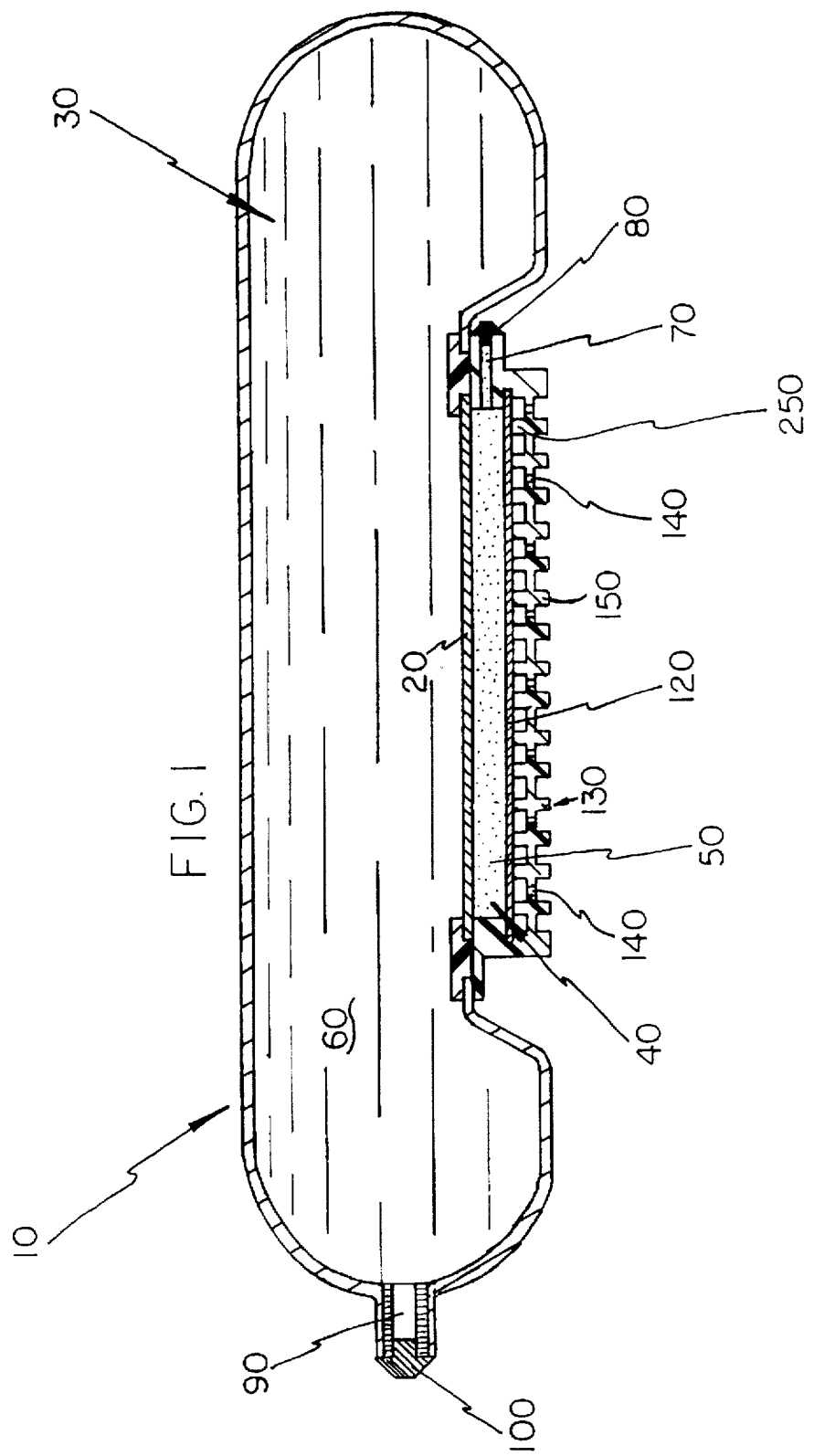
FIG. 1 is a vertical cross-sectional view through a compartmentalized cell culture bag in accordance with the present invention.

REFERENCE NUMERALS IN DRAWINGS 10 compartmentalized cell culture bag
20 membrane
30 basal medium compartment
40 cell culture compartment
50 culture medium
60 basal medium
70 cell culture compartment access port
80 cell culture compartment access port cap
90 basal medium access port
100 basal medium access port cap
120 gas permeable film
130 gas film support
140 gas access opening
150 feet
160 gas access channel
170 gas access channel cover
180 drain port
190 variable oxygen control compartment
200 lower gas permeable film
210 oxygen control compartment bottom
220 oxygen control compartment access port 230 liquid resistor
240 upper membrane support
250 support posts

DETAILED DESCRIPTION

Referring now more specifically to the drawings, FIG. 1 shows a cross-sectional view of a compartmentalized cell culture bag 10. A membrane 20 separates compartmentalized cell culture bag 10 into a basal medium compartment 30 and a cell culture compartment 40. A culture medium 50 containing cells or tissue resides in cell culture compartment 40. A basal medium 60 resides in basal medium compartment 30. Access to cell culture compartment 40 is provided by a cell culture compartment access port 70. Access to basal medium compartment 30 is provided by a basal medium access port 90. A gas permeable film 120 resides on top of a gas film support 130 which is adapted to allow gas, e.g. ambient atmosphere, to contact the vast majority of the surface of gas permeable film 120 by way of gas access openings 140. Feet 150 position the top of gas film support 130 above the surface on which compartmentalized cell culture bag 10 resides.

In operation, basal medium 60 is delivered to basal medium compartment 30 by way of basal medium compartment access port 90. Basal medium access port cap 100 is placed over basal medium access port 90. Membrane 20 is pressed onto the surface of gas permeable film 120 by the weight of basal medium 60. Putting the membrane in this position prior to the introduction of basal medium 60 can also be achieved by generating a vacuum on cell culture compartment 40 by way of cell culture compartment access port 70. A predetermined volume of culture medium 50 containing the desired culture is then introduced into cell culture compartment 40 by way of cell culture compartment access port 70. Cell culture compartment access port cap 80 is placed over cell culture compartment access port 70.

Membrane 20 allows nutrients to pass freely from basal medium 60 to cell culture medium 50 and waste products do pass freely from cell culture medium 50 to basal medium 60. Membrane 20 retains cells and selected compounds in cell culture compartment 40.

Membrane 20 is a material selectively permeable to a class of molecules. Several types of material are acceptable including cellulose, polyacrylontirile, polysulfone, polycarbonate, and polyacrylamide. For example, dialysis membranes retaining molecules and compounds with molecular weights greater than 15,000 are commonly used to culture murine hybridoran cells. By using a membrane with this characteristic, cells, growth factors, and secreted antibodies are retained in cell culture compartment 40. In other applications, it may be advantageous to allow larger molecules and compounds to pass freely between basal medium 60 and culture medium 50. For example, high density culture of lymphocytes may require a large quantity of growth stimulating factors to be present. These factors, such as interleukin 2, can be introduced into basal medium 60 and culture medium 50. By appropriately selecting the pore size of membrane 20, a large source of these factors can be made available to the lymphocytes.

Membrane 20 will not exceed a molecular weight cutoff of 150,000 Daltons in most applications. Yet, there are applications where even larger pore sizes may be desirable. For example, if the purpose is only to culture a large number of cells, any pore size which retains the cells in cell culture compartment 40 can be used. In this case, a 0.2 µM or 0.45 µM microporous polycarbonate membrane such as that commercially available from Poretics Corporation (Livermore, Calif.) could be used.

Gas permeable film 120 is a biocompatible material capable of allowing transfer of gas into and out of cell culture compartment 40. Gas permeable film 120 can be either liquid permeable or impermeable, hydrophobic or hydrophilic, porous or nonporous. Thickness can range above or below 0.25 mm. The best choice depends on the specific application. As a general guideline, the gas permeability of a given membrane should be considered in addition to the interaction of the membrane with either cells or protein structures. Liquid impermeable films of equivalent thickness will establish various steady state oxygen tensions at the cell/gas permeable film interface. FEP Teflon, silicone, and silicone polycarbonate copolymers will establish higher oxygen tension than polyethylene, polycarbonate, polypropylene, polysulfone, or polypropylene films of equivalent thickness. In applications where protein denaturization, non-specific protein binding, cell membrane damage, or cell attachment is affected by the surface chemistry of the film, hydrophilic surfaces are more suitable. In applications where it is desirable to maintain the entire cell membrane in contact with water, hydrated gels may be most suitable.

The use of certain materials not normally associated with gas exchange can expand the options available for controlling oxygen tension at the cell/gas permeable film interface. For example, non-porous cellulose acetate has a relatively low oxygen gas permeability on the order of $7.3 \times 10^{-9}$ $cm^3.cm/(sec.cm^2.atm)$. When cellulose acetate is made porous, it will increase oxygen permeability as it absorbs culture medium 50 with an oxygen permeability of $1.4 \times 10^{-6}$ $cm^3.cm/(sec.cm^2.atm)$. In this manner, varying oxygen tension at the cell/gas permeable film interface of cell culture compartment 40 can be achieved by controlling the amount of culture medium 50 present in gas permeable film 120. Thus, oxygen tension variations will result by varying either the pore size, porosity, or tortuosity of gas permeable film 120.

Figure 2:
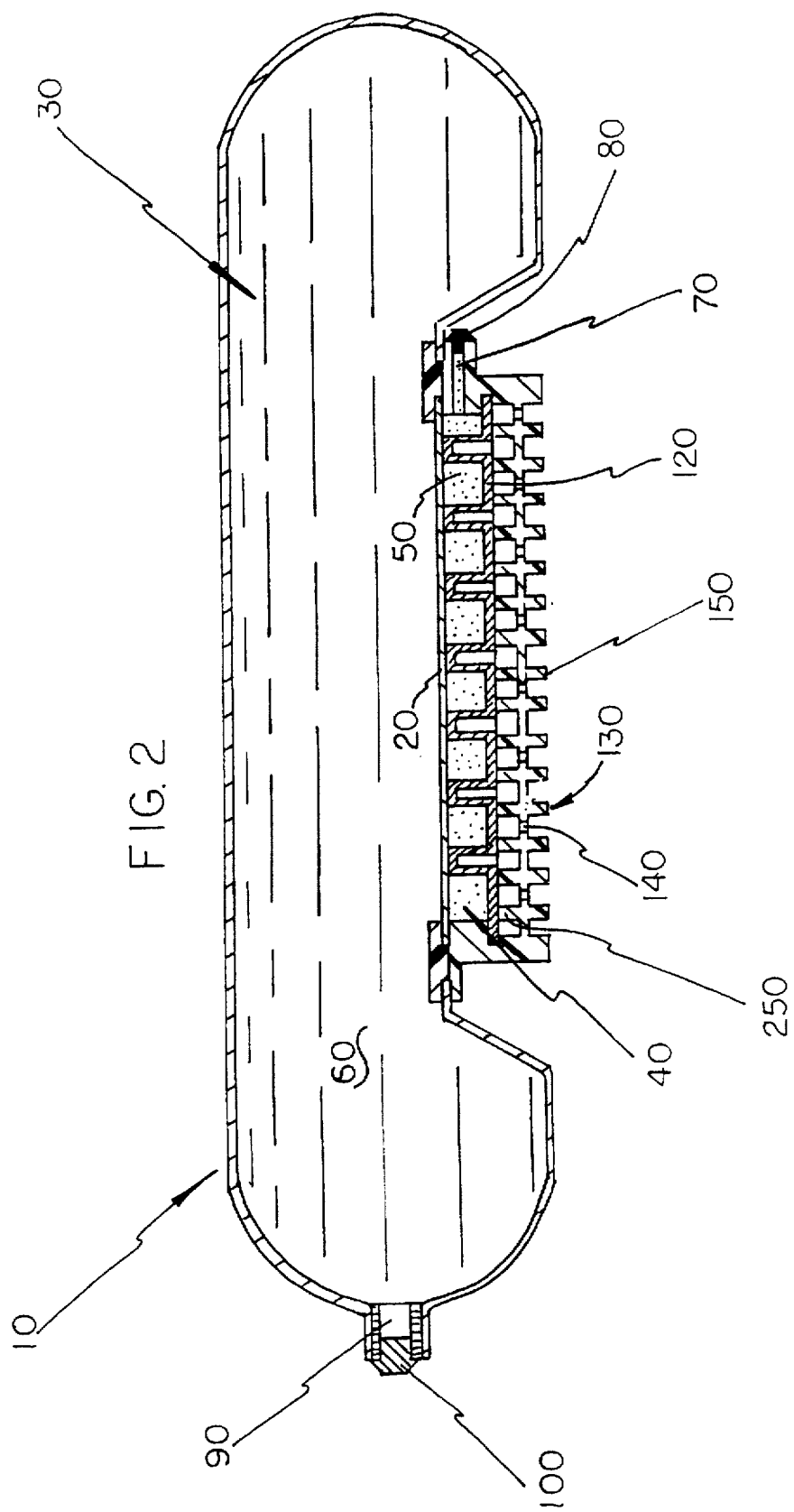
FIG. 2 is a cross-sectional view of a compartmentalized cell culture bag showing an embodiment using gas permeable membrane, portions of which project into the cell culture compartment.

The embodiment of FIG. 2 shows a configuration where portions of gas permeable film 120 project into cell culture compartment 40 to provide additional area for gas transfer. Silicone is a good choice for material as it can be readily molded to form an appropriate shape. Wall thickness can be minimized to allow additional gas transfer into cell culture compartment 40. In the case of silicone, average wall thickness should be kept below about 0.015 inches, preferably between about 0.004 and 0.012 inches.

Gas film support 130 holds gas permeable film 120 in a substantially horizontal position and stabilizes gas permeable film 120 to prevent sagging. Care should be given to assure the flatness of gas permeable film is such that cells do not roll into or otherwise collect in low points. This is an undesirable event as the piling up of cells will create diffusional limitations and lead to cell death. On the other hand, care must also be taken to assure that gas exchange remains adequate. Thus, the amount of contact gas film support 130 makes with gas permeable film 120 will depend on the stiffness and gas permeability of gas permeable film 120 as well as gas exchange and metabolic requirements of a particular cell culture application. It should be expected that most cell lines will become diffusionally limited at about ten to fifteen cell layers.

Gas film support 130 also acts to protect gas permeable film 120 from contamination or puncture. Minimal contact with gas permeable film 120 is made to allow the maximum possible surface area for gas transfer. Gas access opening 140 is sized to allow adequate gas exchange of cell culture compartment 40 while minimizing evaporation. In the preferred embodiment, gas film support 130 is a flexible mesh that can be rolled to allow the compartmentalized bag 10 to be packaged in a minimal volume container. When compartmentalized bag 10 is unrolled for operation, gas film support 130 will provide a structurally stable surface, preventing gas permeable film 120 from sagging under the weight of basal medium 60 and cell culture medium 50.

Figure 3:
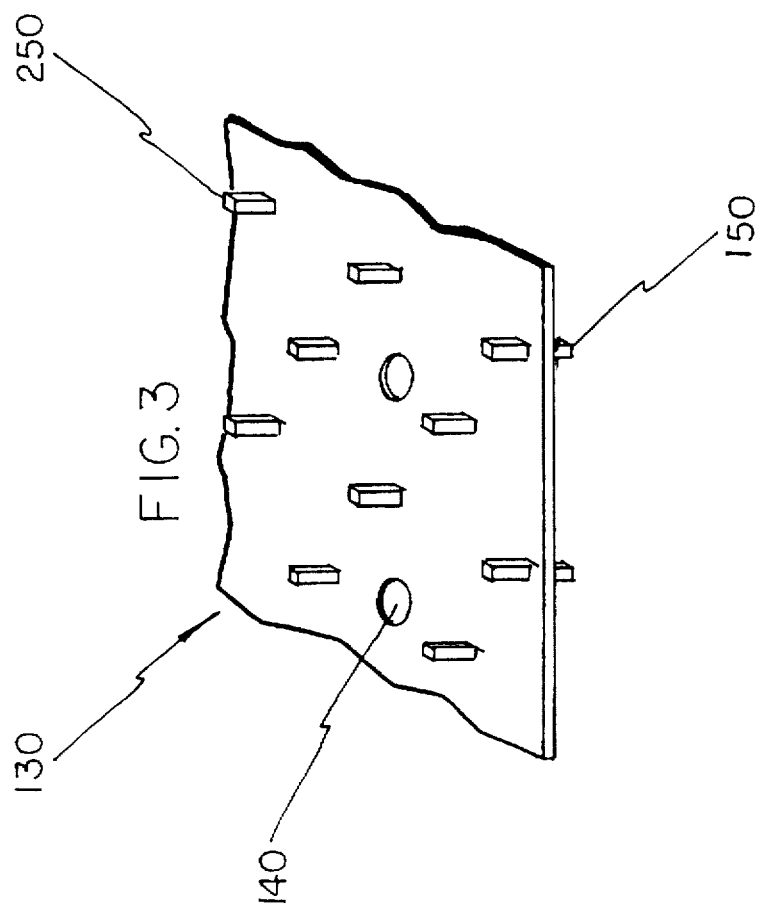
FIG. 3 is a perspective view of a gas film support of FIG. 1 or 2.
Figure 4:
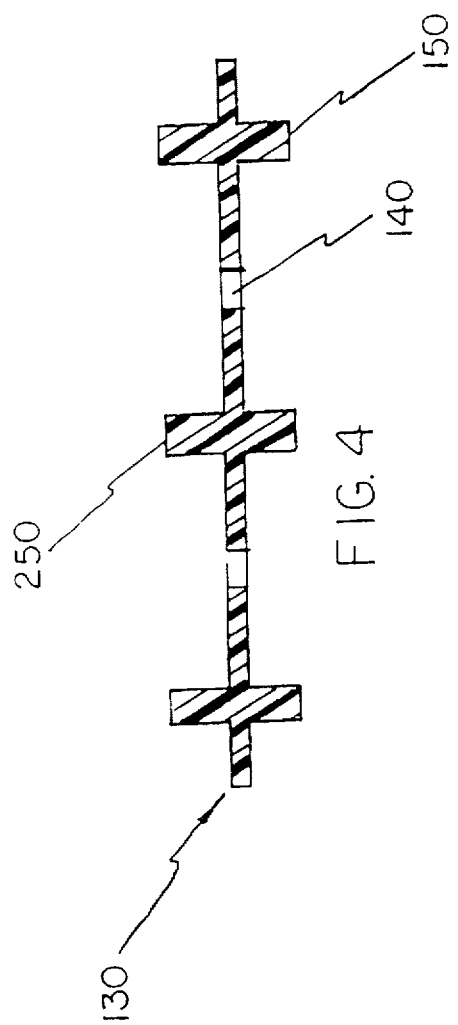
FIG. 4 is a vertical cross-sectional view through the gas film support of FIG. 3.

FIG. 3 and FIG. 4 show an example of how this can be achieved. FIG. 3 is a perspective view of a small section of gas film support 130. FIG. 4 is a cross sectional view of FIG. 3. Feet 150 elevate gas film support 130, allowing transfer through gas access openings 140. Spikes 250 hold gas permeable film 120 in a substantially horizontal position, while transferring the weight of basal medium 60 to feet 150. Fabricating gas film support 130 from a flexible material such as polypropylene will allow gas film support 130 to be rolled when not in operation.

Figure 5:
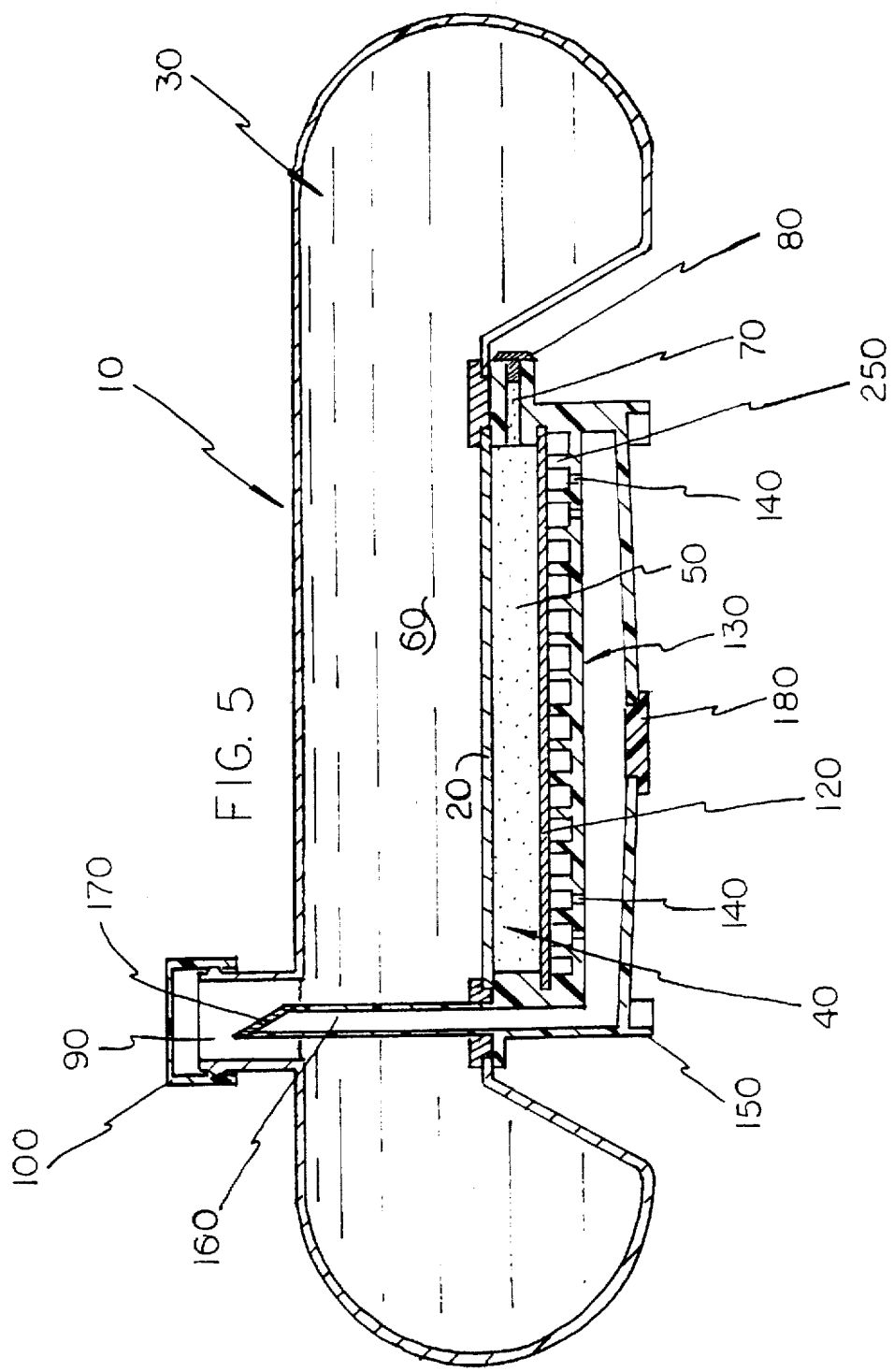
FIG. 5 is a vertical cross-sectional view through an embodiment that controls evaporation of cell culture medium.

Another consideration with regard to material selection for gas permeable film 120 is the moisture vapor transmission rate. Culture medium 50 will evaporate at various rates depending upon the material of the gas permeable film 120. Limiting the cross-sectional area of gas access opening 140 can reduce the rate of evaporation, although the rate of liquid loss will also be a function of the ambient humidity which is more difficult to control. The embodiment of FIG. 5 addresses this issue.

Gas residing between basal medium 60 and the top of basal medium compartment 30 is humidified by basal medium 60. The gas is placed in communication with the underside of gas permeable film 120 by a gas access channel 160. A gas access channel cover 170 is optional. It will prevent basal medium 60 from entering gas access channel 160 and limiting gas transfer. Gas access channel cover 170 is a gas permeable, liquid impermeable film. To prevent condensation from accumulating upon gas access channel cover 170 and diminishing gas transfer, it is not in a horizontal position. Thus, condensation can return to basal medium 60 by gravitational force. Gas access channel 160 is capable of collecting condensation in a drain port 180.

In this embodiment, basal medium access port cap 100 is vented to allow transfer of $O_2$ and $CO_2$ to and from basal medium compartment 30. If the walls of basal medium compartment 30 are highly gas permeable, venting is not required.

Many other methods of placing basal medium head space 170 in communication with gas permeable film 120 are possible. Care should be given to prevent condensation or basal medium 60 from diminishing gas transfer when gas access channel cover 170 is used.

If the types of materials available for gas permeable film 120 do not provide the desired oxygen tension, the configuration shown in FIG. 6 can be utilized. A variable oxygen control compartment 190 is composed of a lower gas permeable film 200 supported in a horizontal position by an oxygen control compartment bottom 210. An oxygen control compartment access port 250 allows a liquid resistor 230 to be introduced into variable oxygen control compartment 190. The oxygen tension at the bottom of gas permeable film 120 can be carefully controlled by varying the height of liquid residing upon a lower gas permeable film 200 in accordance with Fick's Law. Lower gas permeable film 200 can be any highly gas permeable film or sheet. In the preferred embodiment, it is liquid impermeable. Oxygen control compartment bottom 210 allows the vast majority of lower gas permeable film 200 to be in communication with the ambient environment. A hermetic seal exists between lower gas permeable film 200 and oxygen control compartment bottom 210. This seal can be made by welding, adhesives, or any other suitable method. The distance between the top of lower gas permeable film 200 and the bottom of gas permeable film 120 will preferably be between about 5 and 20 mm.

In a preferred embodiment, the volume of culture medium 50 residing in cell culture compartment access port 70 will be a small fraction of the volume of culture medium 50 residing between membrane 20 and gas permeable film 120. It is possible for water from basal medium 50 to move into cell culture compartment 40 if sufficient osmotic gradients develop across membrane 20. This condition can be remedied by utilizing an upper membrane support 240 as shown in FIG. 7. Upper membrane support 240 limits upward travel of membrane 20.

In cases where membrane 20 is comprised of a material such as cellulose that swells or becomes baggy when wet, it also may be desirable to constrain membrane 20 with an upper membrane support 240. Upper membrane support 240 stops upward travel of membrane 20 as culture medium 50 enters cell culture compartment 40. Culture medium 50 presses membrane 20 against upper membrane support 240, smoothing wrinkles.

Wrinkles in membrane 20 can lead to an uneven distribution of cells during inoculation. If membrane 20 were severely wrinkled, culture medium 50 would reside within the wrinkles. Then some areas above gas permeable film 120 would have more culture medium 50 residing above it than others. Cells in the inoculum are distributed equally throughout culture medium 50. Eventually, these cells settle onto gas permeable film 120. Areas of gas permeable film 120 in which a larger volume of culture medium 50 resides above it will receive more cells. Therefore, the wrinkling of membrane 20 should be minimized.

Upper membrane support 240 can be any biocompatible material. In the preferred embodiment, it will be flexible such that compartmentalized cell culture bag can be rolled up when not in operation. Polypropylene will allow this. Care should be given to insure that it does not limit dialysis. In the preferred embodiment, it should be about 70% to 90% open.

Introducing culture medium 50 into cell culture compartment 40 will require enough pressure to overcome the hydrostatic pressure of basal medium 60. This can be accomplished by configuring cell culture compartment assess port 70 to form a hermetic seal with a pipette, syringe, or some other culture medium container such as a bag or bottle. Culture medium 50 can be removed in the same manner.

All of the embodiments prevent evaporation of culture medium 50 from allowing membrane 20 to lose contact with culture medium 50. Membrane 20 is essentially floating on culture medium 50 and as culture medium 50 evaporates through gas permeable film 120, membrane 20 simply gets closer to gas permeable film 120. No dialysis limitation occurs as membrane 20 is always in contact with culture medium 50. If culture medium 50 is reduced by evaporative loss, it can be periodically replenished.

Although there is no restriction on either the shape or size of cell culture compartment 40, the advantageous distance between gas permeable film 120 and membrane 20 is about 1 to 5 millimeters to obtain a high concentration of cells and cell secreted products. When gas permeable film 120 is substantially flat and horizontal, up to about 30×10⁶ cells per square centimeter of surface area can be expected to remain viable. These cells can pile up to a height of about 300 micrometers. Thus, membrane 20 is in no danger of contacting cells and becoming clogged when it resides at least about 1 mm from gas permeable film 120.

In order to minimize the frequency of basal medium 60 exchanges, the volume of basal medium 30 is sized relative to the surface area of gas permeable film 120. For suspension cells that reside in static culture at about one million cells per milliliter, about 5 to 10 ml of basal medium 60 are required for every 1 cm² of gas permeable film 120. When culturing anchorage dependent cells growing in monolayer, advantageously the volume of basal medium 60 (milliliters) exceeds the surface area (square centimeters) of gas permeable film 120 by at least a factor of about two.

Factors that affect the amount of solute mass transfer into and out of cell culture compartment 40 include the surface area of membrane 20. As a general guideline, the surface area of membrane 20 should be approximately equal to the surface area of gas permeable film 120. In applications where only 1 to 2 million moderately metabolically active cells are to be supported per square centimeter of gas permeable film 120, the surface area of membrane 20 can be reduced to about ¼ to ½ of the surface area of gas permeable film 120.

The housing of basal medium compartment 30 can be any flexible, liquid impermeable, biocompatible material. In addition to packaging considerations, the flexible nature of basal medium compensates for the expansion of liquid and gas when the temperature of the fluid in basal medium compartment 30 rises. It is preferable that the housing is optically clear so the medium can be visually monitored for determining the pH of the medium or detecting possible microbial contamination. It is also preferable that the material be gas permeable to allow $CO_2$ transfer to adjust the pH of basal medium 60. Recommendations include polypropylene and polyethylene. Construction of cell culture compartment 40 can be by ultrasonic welding, mechanical fasteners, solvent bonding or any other method which provides leak proof integrity. Gas permeable film 120 and membrane 20 can be sealed by o-rings, gaskets, welding, adhesives, or any other method which provides leak proof integrity. In a preferred embodiment, all materials used in the compartmentalized cell culture bag 10 are compatible with gamma sterilization.

Those skilled in the art will appreciate that numerous modifications can be made thereof without departing from the spirit of the invention. Therefore, it is not intended to limit the breadth of the invention to the embodiments illustrated and described. Rather, the scope of the invention is to be determined by the appended claims and their equivalents.

What is claimed is:

1. A static cell culture device consisting essential of
   a) a container provided with a basal medium access port (90) and an opening,
   b) an upper membrane (20) selectively permeable to compounds of selected sizes and positioned across said opening, said container and said upper membrane (20) together defining a basal medium compartment (30), which includes a flexible wall,
   c) a gas permeable film (120) disposed below said upper membrane (20) and, with said upper membrane (20), defining a cell culture compartment (40),
   d) access means between the inside of said cell culture compartment (40) and outside thereof, whereby cell culture can be introduced into and withdrawn from said cell culture compartment (40), and
   e) a gas film support (130) below and in partial contact with said gas permeable film (120) whereby at least a portion of said gas permeable film (120) is held in a substantially horizontal position such that cells can distribute across the horizontal portion of said gas permeable film (120) and gas can contact the underside of said gas permeable film (120).

2. A device according to claim 1, wherein the surface area of said upper membrane (20) is at least one quarter of the surface area of said gas permeable film (120).

3. A device according to claim 1, wherein the average distance between the substantially horizontal portion of said gas permeable film and said upper sheet is less than about 5 millimeters.

4. A device according to claim 1, wherein the smallest cross-sectional area of said gas film support (130) open to gaseous communication with the ambient environment is less than the total surface area of the underside of said gas permeable film (120) in contact with gas.

5. A device according to claim 1, wherein said gas permeable film includes sections which project into said cell culture compartment (40).

6. A device according to claim 1, wherein said basal medium compartment (30) includes a wall which is gas permeable.

7. A device according to claim 1, including (e) a gas exchange compartment connecting the inside top space of said basal medium compartment (30) with the space below said gas permeable film (120).

8. A device according to claim 7, wherein said gas permeable film (120) includes sections which project into said cell culture compartment (40).

9. A device according to claim 7, wherein said gas exchange compartment prevents basal medium from entering it.

10. A device according to claim 7, including an access port for said gas exchange compartment whereby condensation can be removed and gas other than that of said basal medium compartment (30) can communicate with the underside of said gas permeable film (120).

11. A device according to claim 7, wherein said basal medium compartment (30) includes a wall which is gas permeable.

12. A cell culture device according to claim 1, including
    i) a second gas permeable film (200) disposed in a horizontal position below first said gas permeable film (120),
    ii) means separating first said gas permeable film (120) from said second gas permeable film (200) to form a variable oxygen control compartment (190) adapted to contain fluid, and
    iii) an access port to said variable oxygen control compartment (190), whereby liquid can be added or removed to control the rate of gas transport.

13. A device according to claim 12, wherein first said gas permeable film (120) includes sections which project into said cell culture compartment (40).

14. A device according to claim 12, wherein said basal medium compartment (30) includes a wall which is gas permeable.

15. A method of culturing cells in a device according to claim 1, comprising
    a) introducing a basal medium (60) into said basal medium compartment, b) introducing cells and a cell culture medium (30) into said cell culture compartment (40), and c) maintaining said cell culture compartment (40) at a predetermined temperature, whereby cells proliferate upon the upper surface of said gas permeable film (120) and gas generated within said cell culture compartment (40) passes through said gas permeable film (120).

16. The method according to claim 15, including positively spacing said gas permeable film (120) from a support for the device, thereby providing a gas space below said gas permeable film (120).

17. A method of culturing cells in a device according to claim 12, comprising a) introducing a basal medium (60) into said basal medium compartment (30), b) introducing cells and a cell culture medium (50) into said cell culture compartment (40), c) introducing a liquid into said variable oxygen control compartment (190), and d) maintaining said cell culture compartment (40) at a predetermined temperature.

18. The method according to claim 17, wherein said variable oxygen control compartment (190) is in communication with said basal medium compartment (30), the method including the additional step of introducing basal medium into said oxygen control compartment (190).

\* \* \* \* \*